United States Patent [19]
Morita et al.

[11] Patent Number: 4,746,747
[45] Date of Patent: May 24, 1988

[54] ANISOLE DERIVATIVES

[75] Inventors: Yoshiharu Morita, Yokohama; Naoshi Imaki, Atsugi; Hisao Takayanagi, Yokohama; Yuki Takuma; Tadashi Shirasaka, both of Machida, all of Japan

[73] Assignee: Mitsubishi Chemical Industries Limited, Tokyo, Japan

[21] Appl. No.: 901,367

[22] Filed: Aug. 28, 1986

[30] Foreign Application Priority Data

Sep. 6, 1985 [JP] Japan .................................. 60-197189

[51] Int. Cl.$^4$ .................. C07D 317/48; C07D 405/06; C07D 491/056
[52] U.S. Cl. .................. 549/437; 549/438; 548/454; 546/90
[58] Field of Search .................. 549/437, 438; 548/475, 548/473, 454

[56] References Cited

U.S. PATENT DOCUMENTS 3,922,285 11/1975 Leimgruber et al. .................. 549/437

FOREIGN PATENT DOCUMENTS 0733984 5/1966 Canada .................................. 549/437

Primary Examiner—Nicky Chan
Assistant Examiner—Wendy Davis
Attorney, Agent, or Firm—Oblon, Fisher, Spivak, McClelland & Maier

[57] ABSTRACT

There is provided a novel anisole derivative represented by the following formula (I):

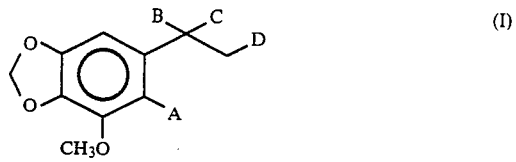

wherein A to D are defined as follows:
(1) A, B and C are each a hydrogen atom, and D represents —OH, a halogen atom, —CO$_2$R$^1$ of which R$^1$ represents a lower alkyl group, —SO$_2$R$^2$ of which R$^2$ represents a lower alkyl group, or

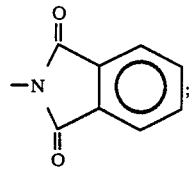

or
(2) A and C are each a hydrogen atom, B is —OH, and D represents —CO$_2$R$^3$ of which R$^3$ represents a lower alkyl group; or
(3) A is a hydrogen atom, B and C form an oxo group =O together, and D represents —CO$_2$R$^4$ of which R$^4$ represents a lower alkyl group; or
(4) B and C are each a hydrogen atom, D is a halogen atom, and A represents —CHO.

13 Claims, No Drawings

ANISOLE DERIVATIVES

This invention relates to a novel anisole derivative useful as an intermediate for the synthesis of cotarnine, a main starting material for the production of tritoqualine which has pharmacological activities, for example, an antiallergic activity (Japanese Patent Application Laid-Open No. 59-44374 and No. 59-44382).

There has been known a method of synthesizing cotarnine by the oxidization of noscapine, one of alkaloids (Yakugaku Zasshi, Vol. 50, 559 (1930)).

However, the starting material noscapine is expensive and has a problem in view of constant supply since it is derived from natural sources.

The present inventors have now found that cotarnine may advantageously be synthesized on an industrial scale by using an anisole derivative as an intermediate compound for the synthesis of cotarnine.

The present invention provides a novel anisole derivative represented by the following formula (I):

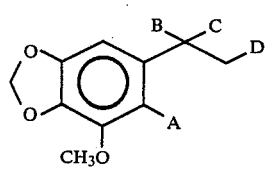

wherein:
(1) A, B and C are each a hydrogen atom, D represents —OH, a halogen atom, —$CO_2R^1$ in which $R^1$ represents a lower alkyl group, —$OSO_2R^2$ in which $R^2$ represents a lower alkyl group, or a group represented by the following formula:

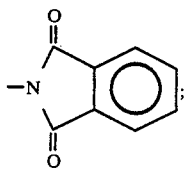

or
(2) A and C are each a hydrogen atom, B is —OH, D represents —$CO_2R^3$ in which $R^3$ represents a lower alkyl group; or
(3) A is a hydrogen atom, B and C form together an oxo group=O, D represents —$CO_2R^4$ in which $R^4$ represents a lower alkyl group; or
(4) B and C are each a hydrogen atom, D is a halogen atom, A represents —CHO.

The invention will now be described more specifically hereinbelow.

In the above definitions for the formula (I), "a lower alkyl group" means the alkyl group having less than 7 carbon atoms, and each of $R^1$ to $R^4$ preferably represents a lower alkyl group having 1 to 5 carbon atoms, and more preferably 1 to 3 carbon atoms.

Illustrative examples of the compounds according to this invention are listed below:

2-(3-methoxy-4,5-methylenedioxyphenyl)ethyl alcohol;
2-(3-methoxy-4,5-methylenedioxyphenyl)ethyl methanesulfonate;
2-(3-methoxy-4,5-methylenedioxyphenyl)ethyl chloride;
2-(3-methoxy-4,5-methylenedioxyphenyl)ethyl bromide;
2-(3-methoxy-4,5-methylenedioxyphenyl)ethyl iodide;
N-[2-(3-methoxy-4,5-methylenedioxyphenyl)ethyl]phthalimide;
methyl 3-(3-methoxy-4,5-methylenedioxyphenyl)propionate;
ethyl 3-(3-methoxy-4,5-methylenedioxyphenyl)propionate;
propyl 3-(3-methoxy-4,5-methylenedioxyphenyl)propionate;
methyl 3-hydroxy-3-(3-methoxy-4,5-methylenedioxyphenyl)propionate;
ethyl 3-hydroxy-3-(3-methoxy-4,5-methylenedioxyphenyl)propionate;
propyl 3-hydroxy-3-(3-methoxy-4,5-methylenedioxyphenyl)propionate;
methyl 3-methoxy-4,5-methylenedioxybenzoylacetate;
ethyl 3-methoxy-4,5-methylenedioxybenzoylacetate;
propyl 3-methoxy-4,5-methylenedioxybenzoylacetate;
2-(2-formyl-3-methoxy-4,5-methylenedioxyphenyl)ethyl chloride;
2-(2-formyl-3-methoxy-4,5-methylenedioxyphenyl)ethyl bromide;
2-(2-formyl-3-methoxy-4,5-methylenedioxyphenyl)ethyl iodide.

A process for preparing compounds of this invention will be described below.

The anisole derivative defined in (1) for the formula (I) wherein D represents —OH, i.e., a derivative of phenylethyl alcohol, may be prepared by reducing the —COOH group of 3-methoxy-4,5-methylenedioxyphenylacetic acid, which is in turn obtained by the hydrolysis of the —CN group of 3-methoxy-4,5-methylenedioxybenzyl cyanide. The starting material, i.e., 3-methoxy-4,5-methylenedioxybenzyl cyanide, may be easily synthesized by a known method (JOC., 13, 886, 1948).

In this reaction scheme, the hydrolysis of the —CN group may be carried out under basic or acidic conditions, which can be applied to any ordinary hydrolysis of —CN groups.

In the case of using basic conditions, the hydrolysis may preferably be conducted in an aqueous solution containing a caustic alkali such as NaOH or KOH. The hydrolysis under acidic conditions may be carried out in an aqueous solution containing a mineral acid such as sulfuric acid or hydrochloric acid. Such an acid or alkali may preferably be used in an excess amount.

The reaction temperature for the hydrolysis is preferably in the range from normal temperature to 150° C.

After the hydrolysis reaction is completed, the reaction mixture may be neutralized and even acidified, resulting in the deposition of a carboxylic acid derivative, which may then be isolated through filtration and washing with water.

The reduction of said carboxylic acid derivatives may be carried out under ordinary reducing conditions for —COOH groups.

As a reducing agent which can be used, mention may be made of i-$Bu_2AlH$, $AlH_3$, $LiAlH_4$, $LiAlH(OCH_3)_3$, $NaAlH_4$, $NaAlH_2(OCH_2CH_2OCH_3)_2$, $NaBH_4$—$AlCl_3$, $NaBH_4$—$BF_3$, $BH_3$, $BH_4$—$(CH_3)_2S$, etc. It is preferred to use such a reducing agent in an excess amount over the carboxylic acid derivative.

Any solvent inert to the reduction may be used, while an ether such as tetrahydrofuran or diethyl ether is preferred.

The reaction temperature in the reduction is preferably in the range from 0° to 100° C.

After the reduction is completed, the reaction mixture is hydrolyzed and extracted, followed by distilling off the solvent of the extracted layer to give the final product, derivative of phenylethyl alcohol.

Alkanesulfonic acid esters, i.e., the anisole derivatives defined in (1) for the formula (I) wherein D represents $-OSO_2R^2$, may be obtained by reacting a compound of the following formula (II):

$$R^2OSO_2X \qquad (II)$$

wherein $R^2$ is as previously defined for the formula (I) and X is a halogen atom, with the derivative of phenylethyl alcohol.

Examples of the compounds of the formula (II) include methanesulfonyl chloride, methanesulfonyl bromide, methanesulfonyl iodide, ethanesulfonyl chloride, ethanesulfonyl bromide, ethanesulfonyl iodide, propanesulfonyl chloride, propanesulfonyl bromide and propanesulfonyl iodide. Such a compound is preferably used in an excess amount over the derivative of phenylethyl alcohol.

In this reaction, it is preferred to use a dehydrohalogenating agent. A preferable example of such agents is a tertiary amine such as triethylamine, tripropylamine, tributylamine, pyridine or quinoline. Such a dehydrohalogenating agent may be preferably used in an excess amount over the derivative of phenylethyl alcohol.

Any solvent inert to the reaction may be used. The reaction temperature is preferably in the range from $-20°$ C. to 100° C.

After completion of the reaction, the reaction mixture is hydrolyzed and extracted, and then the solvent of the extracted layer is distilled off to give the final product, alkanesulfonic acid ester.

The anisole derivatives defined in (1) for the formula (I) wherein D represents a halogen atom may be obtained by reacting the derivative of phenylethyl alcohol with a halogenating agent.

In this reaction, a halogen atom will be substituted for the alcoholic hydroxyl group in the derivative of phenylethyl alcohol. As the halogenating agent, there may be used, for example, a hydrogen halide such as HCl, HBr or HI; a phosphorus halide such as $PCl_3$, $PBr_3$ or $PF_3$; $SOCl_2$, $COCl_2$, or for the like. Such a halogenating agent may preferably be used in an excess amount over the derivative of phenylethyl alcohol.

Any solvent inert to the halogenating reaction may be used. The reaction temperature is preferably between $-10°$ C. and 100° C.

After the reaction is completed, the reaction mixture is hydrolyzed and extracted, and then the solvent of the extracted layer is distilled off to obtain the final halogenated product to be desired.

Alternatively, these halogenated products may also be obtained by reacting a metal halide with said alkanesulfonic acid ester. As a metal halide which can be used in the reaction, mention may be made of, for example, NaCl, NaBr, NaI, KCl, KBr, KI, or the like. Such a halide is preferably used in an excess amount over the alkanesulfonic acid ester.

The reaction temperature is preferably from normal temperature to 160° C., and any solvent inert to this reaction may be used.

After the reaction is over, the reaction mixture is cooled and the deposited salt is separated, followed by distilling off the solvent to obtain the final halogenated product, which may further be purified by column chromatography.

The anisole derivative as defined in (1) for the formula (I) wherein D represents the group of the following formula:

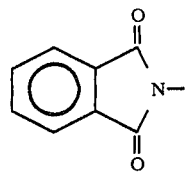

may be obtained by reacting a compound represented by the following formula (III):

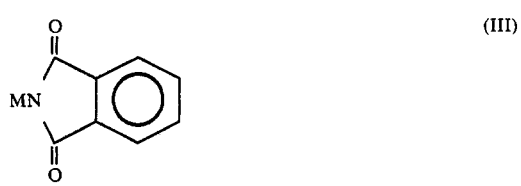

wherein M represents an alkali metal with said halogenated product.

An example of the alkali metal represented by M is Na, Li or the like, which is preferably used in a proportion of 0.5 to 2.0 moles per mole of the halogenated product.

A polar solvent may preferably be used as a solvent in the reaction, and the reaction temperature is preferably in the range of from normal temperature to 160° C.

After completion of the reaction, the reaction mixture is hydrolyzed and extracted, and then the solvent of the extracted layer is distilled off to obtain the final product to be desired.

The benzoylacetic acid esters as defined in (3) for the formula (I) may be obtained by reacting an acetic acid ester represented by the following formula (V):

$$CH_3COOR^3 \qquad (V)$$

wherein $R^3$ is as previously defined for the formula (I), with a benzoic acid ester represented by the following formula (IV):

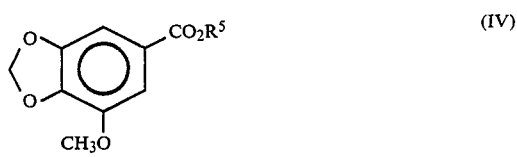

wherein $R^5$ represents an alkyl group having 1 to 5 carbon atoms, in the presence of a base.

This reaction is called Claisen condensation and generally described in the literature (Org. React., 1, 266, 1942). The benzoic acid esters represented by the formula (IV) which are used as starting materials in this reaction are known compounds and may be easily synthesized according to the method shown in the literature (Z. Naturforsch., 33C, 465, 1978).

The bases used in the Claisen condensation may include, for example, alkoxides of alkali metals such as MeONa, EtONa, n-PrONa, i-PrONa, i-BuONa, sec-BuONa, t-BuONa, EtOK and MeOK; hydroxides of alkali metals such as NaOH, KOH and LiOH; and hydrides of alkali metals such as NaH, KH and LiH. Such a base is preferably used in an excess amount over the benzoic acid ester. It is noted that Me, Et, Pr and Bu mean methyl, ethyl, propyl and butyl respectively.

Any solvent inert to the reaction may be used. The temperature for the Claisen condensation may be in the range from normal temperature to 120° C.

After the reaction is completed, the reaction mixture is hydrolyzed and extracted, followed by distilling off the solvent of the extracted layer and recrystallization of the residue to give the final, benzoylacetic acid ester.

The 3-hydroxy-3-phenylpropionic acid esters as defined in (2) for the formula (I) may be obtained by reducing the ketone group of said benzoylacetic acid esters.

The reducing reaction may be conducted under conditions which are generally used to reduce ketones into secondary alcohols. This reaction may be performed either in a stoichiometrical reduction method in which a reducing agent is used in a stoichiometrical amount or in a catalytic reduction method in which the reduction is conducted using a catalyst under hydrogen.

In the former method, a reducing agent such as, for example, $NaBH_4$ or $B_2H_6$ may be used, preferably, in an excess amount over the starting ketone. Any solvent may be used for the reaction, but an alcohol such as methanol or ethanol is preferred. Upon completion of the reaction, the reaction mixture is hydrolyzed and extracted, followed by distilling off the solvent of the extracted layer to obtain the final product, 3-hydroxy-3-phenylpropionic acid ester.

In the latter method, a catalyst such as, for example, Pt black, Pt/C, Pt/alumina, Pd black, Pd/C or Pd/alumina may preferably be used. The amount thereof used is preferably in the range of 0.0001 to 10% per mole based on the starting ketone. Hydrogen may be at normal pressure or in the pressurized state. Any solvent inert to the reduction may be used. The reaction temperature is preferably from normal temperature to 100° C. After the reaction is completed, the reaction mixture is filtered to remove the catalyst. The filtrate is extracted and then the solvent is distilled off to obtain the final product, 3-hydroxy-3-phenylpropionic acid ester.

The phenylpropionic acid esters as defined in (1) for the formula (I) wherein D represents $-COOR^1$ may be obtained by hydrogenating said benzoylacetic acid esters as defined in (3) for the formula (I) or said 3-hydroxy-3-phenylpropionic acid esters as defined in (2) for the formula (I). This reaction is one of ordinary hydrogenolytic reactions of benzyl alcohols and phenyl ketones and may be conducted in the presence of hydrogen and a catalyst.

The catalyst used in the hydrogenation may be $PtO_2$, Pt black, Pt/C, Pt/alumina, Pd black, Pd/C, Pd/alumina or the like, which may preferably be used in an amount of 0.0001 to 10% per mole based on the starting compound.

Hydrogen may be used either at normal pressure or in the pressurized state. Any solvent inert to this reaction may be used.

This reaction may be promoted by the presence of an acid, which may include, for example, a mineral acid such as sulfuric acid or hydrochloric acid and an organic acid such as acetic acid or p-toluenesulfonic acid. Such an acid may preferably be used in an excess amount over the starting compound.

The reaction temperature is in the range of from normal temperature to 160° C.

After completion of the reaction, the catalyst is separated from the reaction mixture and the solvent is distilled off to give the final product, phenylpropionic acid ester.

The formylated products as defined in (4) for the formula (I) may be obtained by formylating said halogenated products.

This formylating reaction is called Vilsmeier reaction in which a formamide compound and a condensating agent are utilized. The formamide compound may preferably include dimethylformamide, N-methylformanilide and the like. The condensating agent may preferably be $POCl_3$, $COCl_2$, $SOCl_2$ or the like.

Such a formamide compound and condensating agent are preferably used in a proportion of 1.0 to 10 moles per mole of the halogenated product to be used.

Any solvent inert to this reaction may be used, and the reaction temperature is preferably from normal temperature to 160° C.

The reaction may be carried out according to any of the following three methods: (a) the reaction of a halogenated product with a pre-formed Vilsmeier complex of a formamide compound and a condensating agent; (b) the simultaneous reaction of a formamide compound, a condensating agent and a halogenated product; and (c) the addition of any one of the three reactants to the reaction mixture comprising the remaining two.

After the reaction is over, the reaction mixture is hydrolyzed and extracted and then the solvent of the extracted layer is distilled off to obtain a crude product. The crude product contains isomers in which a formyl group is attached to the undesired position. The desirable formylated product may be obtained by separating the same from the other isomers by column chromatography or recrystallization from an alcohol-water solvent.

The thus obtained compounds according to this invention may serve as a useful intermediate for the preparation of cotarnine.

The route for the synthesis of cotarnine from the compounds of this invention may be schematically illustrated below.

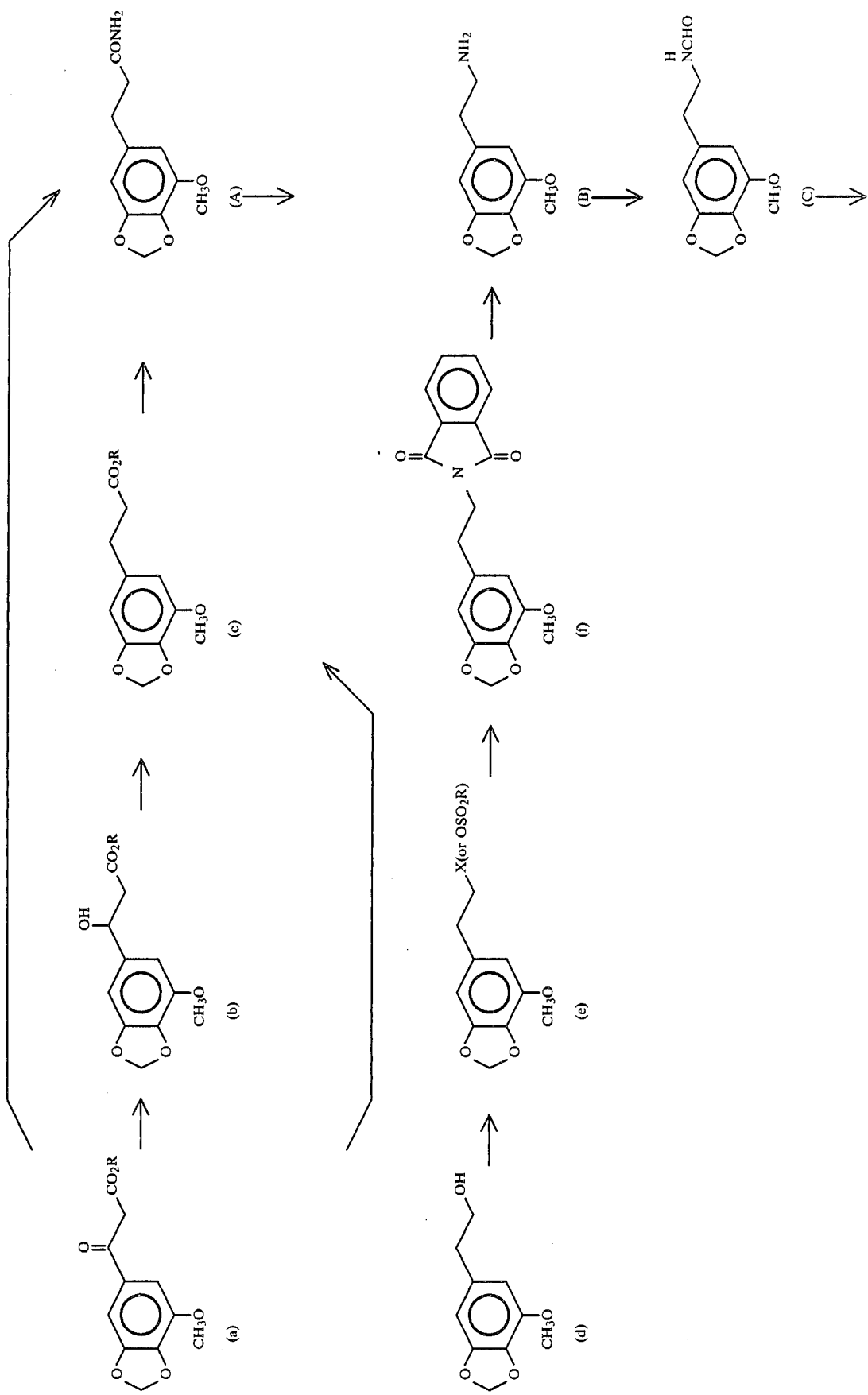

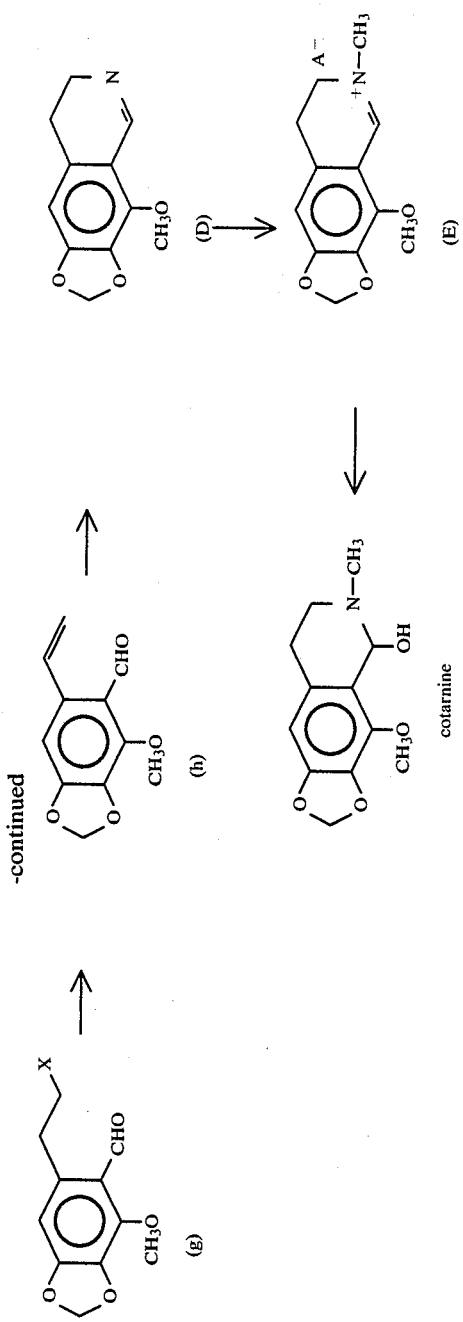

In the formulae of the above-illustrated reaction scheme, R represents a lower alkyl group, X represents a halogen atom, and A⁻ represents an anion.

In the above reaction scheme, the route of (A)→(B) →(C)→(D)→(E)→cotarnine and the compounds (A), (B), (C), (D) and (E) are known (Ann., 395, 328 (1912); JACS, 70, 2887 (1948)).

Compound (A) may be prepared by reacting a phenylpropionic acid ester (c) with ammonia. Ammonia may preferably be used in an excess amount over the phenylpropionic acid ester (c). The reaction may be carried out under normal pressure or in a pressurized state and at a temperature in the range of from normal temperature to 160° C.

A benzoylacetic acid ester (a) may be converted into its corresponding amide, i.e., compound (A), by the in situ reaction thereof with ammonia under a reductive condition, followed by distilling off excess ammonia and the solvent used.

Compound (B) may be prepared by reducing the N-phenylethyl-phthalimide (f) with hydrazine, which may be used in an excess amount over the phthalimide (f). The reaction temperature is preferably from normal temperature to 150° C. After the reaction is over, the reaction mixture is hydrolyzed so as to make it basic and then extracted, followed by distilling off the solvent of the extracted layer and recrystallization to give compound (B).

2-Methoxy-3,4-methylenedioxy-6-vinylbenzaldehyde (h) may be prepared by dehydrohalogenating a 2-(2-formyl-3-methoxy-4,5-methylenedioxyphenyl)ethyl halide (g). The dehydrohalogenating reaction may proceed under heating, but it may be promoted in the presence of a dehydrogenating agent, which may include, for example, tertiary amines such as triethylamine, pyridine and quinoline. The compound (h) may be converted into compound (D) by reacting it with ammonia according to a known method (Chem. Ber., 103, 3605, 1970).

Examples

The present invention will now be described more specifically with reference to the following examples, but these examples are not to be construed to restrict the scope of the invention.

EXAMPLE 1

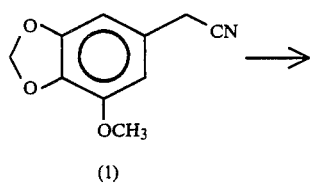

(1)

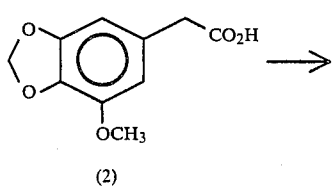

(2)

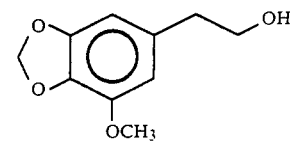

(3)

27.55 g (0.144 mol) of 3-methyoxy-4,5-methylenedioxy benzylcyanide (1) and 30.3 g (0.72 mol) of 95% sodium hydroxide aqueous solution were added to a mixture of 29 ml of water and 29 ml of 2-methoxyethanol, and the mixture was refluxed under heating for 3.5 hours. The reaction mixture was cooled, added with 145 ml of water and then further added portionwise with concentrated hydrochloric acid to make the reaction mixture acidic. The deposited crystal was filtered out, washed with 2×40 ml of water and then dried under vacuum at 60° C. to obtain 34.09 g of a crude crystal of 3-methoxy-4,5-methylenedioxyphenylacetic acid (2).

7.30 g (0.192 mol) of lithium alminium hydride was added to 270 ml of anhydrous tetrahydrofuran, and to this solution was added portionwise 33.68 g of 3-methoxy-4,5-methylenedioxyphenylacetic acid (2) with stirring under water-cooling. The mixture was stirred at room temperature for one hour, then added with 2.0 g (53 mmol) of lithium aluminium hydride and further stirred for one hour. The reaction mixture, while being cooled in an ice bath, was added portionwise with a solution of 9.3 ml of water and 10 ml of tetrahydrofuran and then further added portionwise with 9.3 ml of 15% sodium hydroxide aqueous solution. The resulting mixture was further added with 27.9 ml of water and then 500 ml of ethyl ether followed by stirring for 30 minutes. The deposited salt was filtered out and washed with ethyl ether. The filtrate and the ethyl ether used for washing were joined and concentrated under reduced pressure, and the residual oil was distilled in vacuo to obtain 19.09 g of 2-(3-methoxy-4,5-methylenedioxyphenyl)ethyl alcohol (3) as an oil. Boiling point: 140°–142° C./ 1 mmHg: yield 68.4%.

The identification data of the resultant product are as follows:

IR (neat, $\nu$max cm⁻¹): 1635, 1515, 1140, 1100, 1050.

¹H-NMR (60 MHz, in CDCl₃, δppm): 1.87 (1H, s, —OH), 2.70 (2H, s, J=6 Hz, ArCH₂CH₂OH), 3.74 (2H, s, J=6 Hz, ArCH₂CH₂OH), 3.83 (3H, s, OCH₃), 5.87 (2H, s,

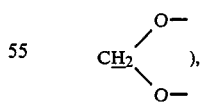

), 6.35 (2H,s,

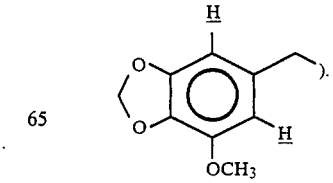

).

EXAMPLE 2

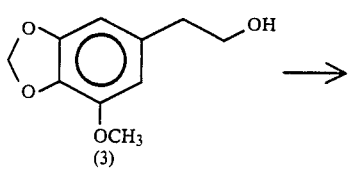

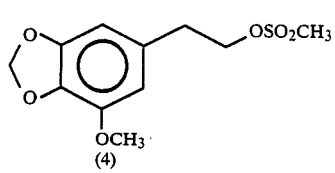

3.92 g (20 mmol) of 2-(3-methoxy-4,5-methylenedioxyphenyl)ethyl alcohol (3) and 3.06 ml (22 mmol) of triethylamine were dissolved in 40 ml of methylene chloride, and to this mixture was added portionwise 1.70 ml (22 mmol) of methanesulfonyl chloride under ice-cooling. The mixture was stirred for one hour followed by addition of 20 ml of water and then the mixture was separated. The methylene chloride layer was washed with 20 ml of water and dried over anhydrous magnesium sulfate. The solvent was distilled off under reduced pressure to obtain 5.45 g of 2-(3-methoxy-4,5-methylenedioxyphenyl)ethyl methanesulfonate (4) as a crystal (yield: 99%), which was recrystallized from toluene. Boiling point: 78°-80° C.

The identification data of the resultant product are as follows:

IR (KBr, νmax cm⁻¹): 1350, 1180, 1140, 1100, 960.

¹H-NMR (60 MHz, in CDCl₃, δppm): 2.85 (3H, s, SO₂CH₃), 2.90 (2H, t, J=7 Hz, ArCH₂CH₂OSO₂CH₃), 3.83 (3H, s, OCH₃), 4.31 (2H, t, J=7 Hz, ArCH₂CH₂OSO₂CH₃), 5.87 (2H,s,

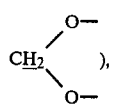

6.33 C2H,S,

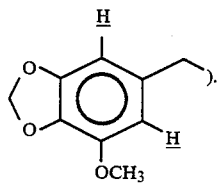

EXAMPLE 3

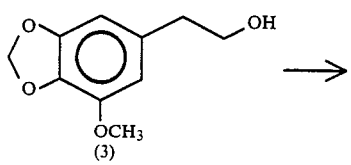

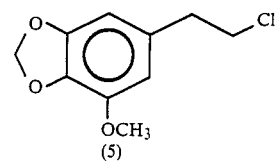

3.92 g (20 mmol) of 2-(3-methyoxy-4,5-methylenedioxyphenyl)ethyl alcohol (3) and 1.94 ml (24 mmol) of pyridine were dissolved in 40 ml of toluene, and to this mixture was added portionwise 1.74 ml (24 mmol) of thionyl chloride in 5 ml of toluene under cooling with water. The mixture was heated to 60° C. for 2 hours, then cooled and washed with 30 ml of water, 20 ml of water, 30 ml of a saturated sodium hydrocarbonate aqueous solution and 30 ml of a saturated saline solution successively in this order. This reaction mixture was then dried over anhydrous sodium sulfate and decolored by active carbon. The solvent was distilled off to obtain 4.05 g of 2-(3-methoxy-4,5-methylenedioxyphenyl)ethyl chloride (5) as a crystal with a yield of 94%, which was recrystallized from n-hexane. Melting point: 67°-68° C.

The identification data of the resultant product are as follows:

IR (KBr, νmax cm⁻¹): 1510, 1315, 1195, 1130, 1095, 1040.

¹H-NMR (60 MHz, in CDCl₃, δppm): 2.96 (2H, t, J=7 Hz, ArCH₂CH₂Cl), 3.67 (2H, t, J=7 Hz, ArCH₂CH₂Cl), 3.90 (3H, s, OCH₃), 5.93 (2H, s,

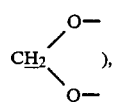

6.38 (2H,s,

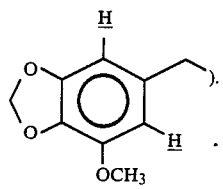

EXAMPLE 4

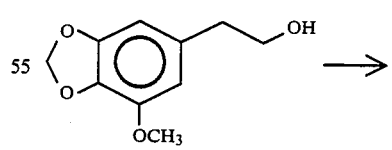

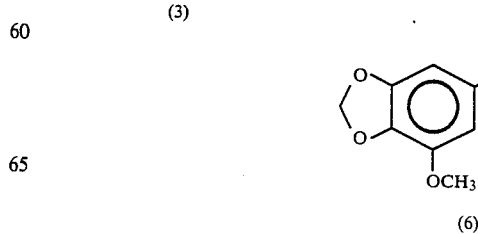

2.74 g (14 mmol) of 2-(3-methoxy-4,5-methylenedioxyphenyl)ethyl alcohol (3) was dissolved in 10 ml of ethyl ether, to which was added portionwise 1.64 g (6.1 mmol) of phosphorus tribromide in 2 ml of ethyl ether under ice-cooling. The mixture was refluxed under heating for one hour, then cooled and further stirred while adding 10 ml of water and 15 ml of a saturated sodium hydrogencarbonate aqueous solution. The reaction mixture was separated and the ether layer was washed with 10 ml of a saturated saline solution, dried over anhydrous magnesium sulfate and concentrated under reduced pressure. The residue was purified by silica column chromatography (eluate: ethyl acetate / n-hexane=½) to obtain 1.93 g of 2-(3-methoxy-4,5-methylenedioxyphenyl)ethyl bromide (6) as a crystal with a yield of 53%. Melting point: 78°-79° C.

The identification data of the resultant product are as follows:

IR (KBr, νmax cm⁻¹): 1310, 1200, 1140, 1095, 1045.

¹H-NMR (60 MHz, in CDCl₃, δppm): 3.03 (2H, t, J=7 Hz, ArCH₂CH₂Br), 3.50 (2H, t, J=7 Hz, ArCH₂CH₂Br), 3.87 (3H, s, OCH₃), 5.90 (2H, s,

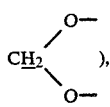), 6.35 (2H, s,

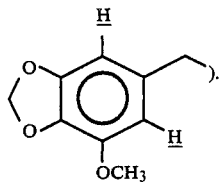).

EXAMPLE 5

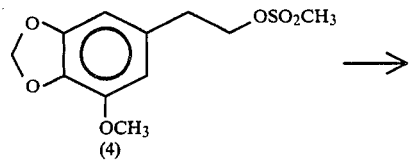

5.45 g (19.9 mmol) of 2-(3-methoxy-4,5-methylenedioxyphenyl)ethyl methanesulfonate (4) and 3.58 g (23.9 mmol) of sodium iodide were added to 100 ml of acetone and refluxed under heating for 2 hours. To this reaction mixture was added again 0.89 g (5.9 mmol) of sodium iodide, and the reaction mixture was refluxed under heating for 3 hours and 20 minutes. After the refluxed mixture was cooled, the deposited salt was filtered out and washed with acetone. The filtrate and the acetone used for washing were combined and concentrated under reduced pressure. The residue was purified by silica gel chromatography (eluate: ethyl acetate n-hexane=½) to obtain 5.80 g of 2-(3-methoxy-4,5-methylenedioxyphenyl) ethyl iodide (7) as a crystal with a yield of 95%, which was recrystallized from n-hexane/ethyl acetate. Melting point: 78°-80° C.

The identification data of the resultant product are as follows:

IR (KBr, νmax cm⁻¹): 1630, 1135, 1095.

¹H-NMR (60 MHz, in CDCl₃, δppm): 2.9-3.5 (4H, m, ArCH₂CH₂I), 3.85 (3H, s, OCH₃), 5.88 (2H, s,

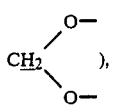), 6.30 (2H, s,

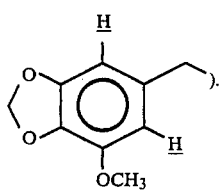).

EXAMPLE 6

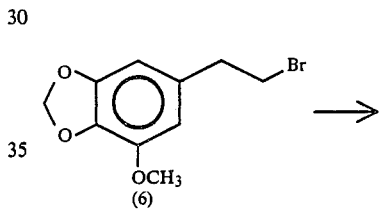

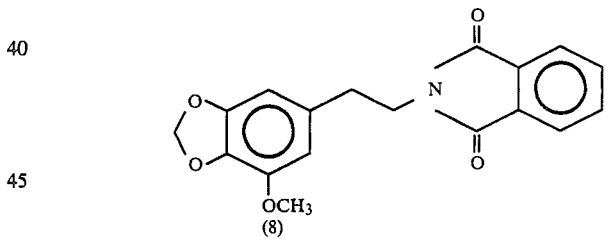

518 mg (2mmol) of 2-(3-methoxy-4,5-methylenedioxyphenyl) ethyl bromide (6) and 370 mg (2 mmol) of potassium phthalimide were added to 4 ml of N,N-dimethylformamide and stirred under heating at 60° C. for 2 hours. After cooling, the reaction mixture was stirred for 15 minutes while adding 20 ml of water. The deposited crystal was filtered out, washed with water and then dried to obtain 597 mg of N-[2-(3-methoxy-4,5-methylenedioxyphenyl)ethyl]ethyl]phthalimide (8) (yield: 92%), which was recrystallized from ethyl acetate. Melting point: 169°-170° C.

The identification data of the resultant product are as follows:

IR (KBr, νmax cm⁻¹): 1720, 1395, 1110.

¹H-NMR (60 MHz, in CDCl₃, δppm): 2.87 (2H, t, J=7 Hz, ArCH₂CH₂N), 3.80 (3H, s, OCH₃), 3.88 (2H, t, J=7 Hz, ArCH₂CH₂N), 5.88 (2H, s,

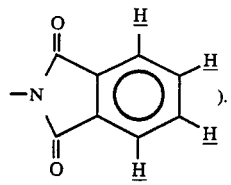, 6.37 (1H, s, 6.40 (1H, s, 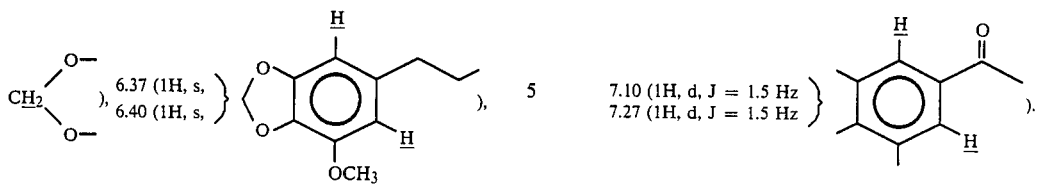), 7.5–8.0 (4H, m, 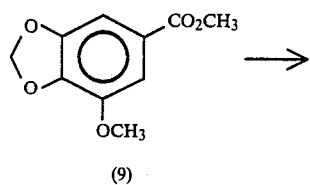).

EXAMPLE 7

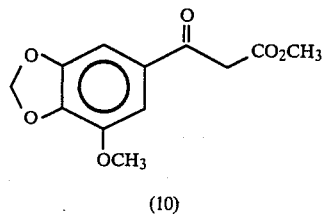

(9)

→

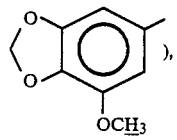

(10)

2.08 g (52 mmol) of 60% NaH was suspended in 8 ml of N,N-dimethylformamide (DMF) containing 4.20 g (20 mmol) of methyl 3-methoxy-4,5-methylenedioxybenzoate (9), and to this mixture was added dropwise with stirring 2.8 ml (35 mmol) of methyl acetate in 3 ml of dimethylformamide at such a rate that the temperature of the reaction mixture could be maintained at 50°–60° C. After this addition was over, the reaction mixture was kept at 55° C. for one hour, then cooled to room temperature and added with 3.8 ml of acetic acid to stop the reaction. The reaction mixture was added with 30 ml of ice-cold water and extracted with toluene (15 ml×2). The toluene layer was washed with water, further washed with a saturated sodium hydrogencarbonate aqueous solution, then dried over anhydrous magnesium sulfate and concentrated. The residue was washed several times with a small quantity of n-hexane and recrystallized from methanol (10 ml) to obtain 3.61 g of methyl 3-methoxy-4,5-methylenedioxybenzoylacetate (10) (yield: 71.6%). Melting point: 65.5°–66.5° C.

The identification data of the resultant product are as follows:

IR (KBr, disk, νmax cm$^{-1}$): 1760, 1675, 1625, 1335, 1150, 1095.

$^1$H-NMR (100 MHz, in CDCl$_3$, δppm): 3.75 (3H, s, —CO$_2$CH$_3$), 3.92 (2H, s, COCH$_2$), 3.95 (3H, s, ArOCH$_3$), 6.07 (2H, s, —OCH$_2$O—), 7.10 (1H, d, J = 1.5 Hz 7.27 (1H, d, J = 1.5 Hz 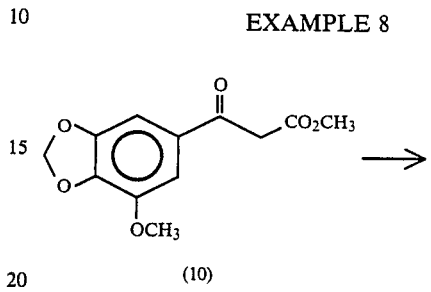).

EXAMPLE 8

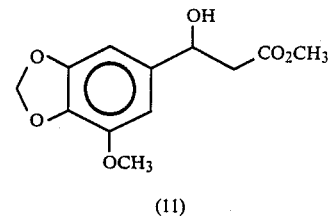

(10)

→

OH
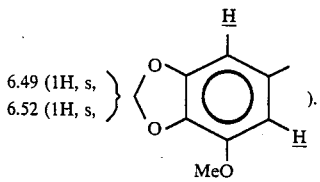 CO$_2$CH$_3$ (11)

200 mg of methyl 3-methoxy-4,5-methylenedioxybenzoylacetate (10) was suspended together with 20 mg of 5% Pd/C in 5 ml of methanol and subjected to hydrogenation at normal temperature and pressure. After the absorption of a predetermined amount of hydrogen was ascertained, the reaction mixture was filtered to remove the catalyst and then washed with methanol. On concentrating the filtrate, there was obtained 202 mg of methyl 3-hydroxy-3-(3-methoxy-4,5-methylenedioxyphenyl)propionate (11) as an oil with a quantitative yield.

The identification data of the resultant product are as follows:

IR (neat, νmax cm$^{-1}$): 3500, 1735, 1635, 1515, 1435, 1130.

$^1$H-NMR (100 MHz, in CDCl$_3$, δppm): 2.5–2.9 (2H, m, —CH$_2$CO$_2$CH$_3$), 3.48 (1H, d, J=3 Hz, —OH), 3.69 (3H, s, —CO$_2$CH$_3$), 3.87 (3H, s,

), 4.9–5.1 (1H, m, —CHOHCH$_2$—), 5.91 (2H, s, —OCH$_2$O—), 6.49 (1H, s, 6.52 (1H, s, ).

EXAMPLE 9

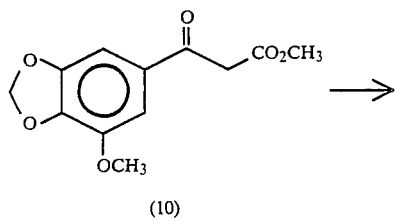

(10)

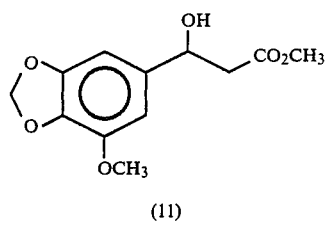

(11)

252 mg of methyl 3-methoxy-4,5-methylenedioxybenzoylacetate (10) dissolved in 15 ml of methanol was reduced by 20 mg of sodium boron hydride. After the reduction was completed, methanol was distilled off and the residue was added with water and extracted with ethyl ether. The ethyl ether layer was washed with water, dried over anhydrous magnesium sulfate, filtered and concentrated to obtain 255 mg of methyl 3-hydroxy-3-(3-methoxy-4,5-methylenedioxyphenyl)propionate (11) with a quantitative yield.

EXAMPLE 10

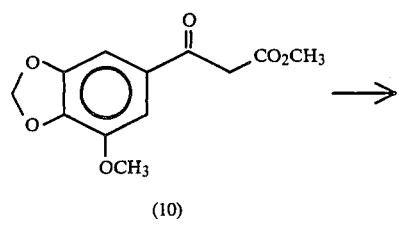

(10)

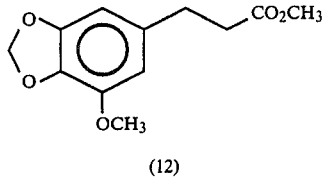

(12)

550 mg of methyl 3-methoxy-4,5-methylenedioxybenzoylacetate (10) and 55 mg of 5% Pd/C were suspended in 10 ml of methanol containing 2 drops (about 50 mg) of concentrated sulfuric acid. The mixture was subjected to hydrogenation at normal temperature and pressure. It was confirmed by thin layer chromatography that the hydrogenation was completed when twice as much moles of hydrogen as the starting material had been absorbed. After the catalyst was filtered out and washed, the filtrate was concentrated. The resultant residue was dissolved in 15 ml of ethyl ether, then dried over anhydrous magnesium sulfate, again filtered, washed with Et$_2$O and concentrated to obtain 519 mg of pure methyl 3-(3-methoxy-4,5-methylenedioxyphenyl)propionate (12) with a quantitative yield.

The identification data of the resultant product are as follows:

IR (neat, νmax cm$^{-1}$): 1740, 1635, 1515, 1195, 1135.

$^1$H-NMR (100 MHz, in CDCl$_3$, δppm): 2.4–3.0 (4H, m, —C$\underline{H}_2$C$\underline{H}_2$CO$_2$CH$_3$), 3.67 (3H, s, —CO$_2$C$\underline{H}_3$), 3.87 (3H, s,

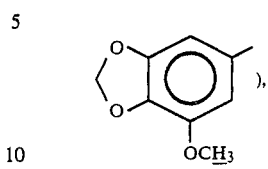

), 5.90 (2H, s, —OC$\underline{H}_2$O—), 6.34 (2H, s,

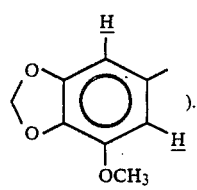

).

EXAMPLE 11

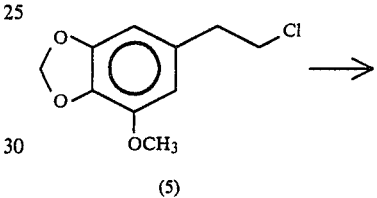

(5)

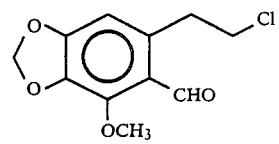

(13)

3.18 ml of phosphorus oxytrichloride was added dropwise to 27 ml of dimethylformamide at room temperature, and the mixture was stirred for 30 minutes so as to synthesize a Vilsmeier complex. To this complex 3.0 g of 2-(3-methoxy-4,5-methylenedioxyphenyl)ethyl chloride (5) was added and stirred in an oil bath at 100° C. for 9 hours. The reaction mixture was cooled to room temperature, then poured into about 100 ml of water and perfectly hydrolyzed by excess sodium acetate. Then the reaction mixture was extracted with ethyl acetate and the ethyl acetate layer was washed with water and dried. Distillation off the solvent gave 3.31 g of a crude crystal (rough yield: 98%), which was dissolved in about 100 ml of n-hexane with stirring under heating, and then the soluble in the n-hexane was taken out. This operation using n-hexane was repeated three times and finally n-hexane was distilled off to obtain 2.71 g of an almost pure light-yellow crystal with a yield of 80%.

The NMR spectra of the resultant crystal showed that this product was a mixture of 2-(2-formyl-3-methoxy- 4,5-methylenedioxyphenyl)ethyl chloride and 2-(6-formyl-3-methoxy-4,5-methylenedioxyphenyl)ethyl chloride in a mole ratio of 7:3. 2-(2-formyl-3-methoxy-4,5-methylenedioxyphenyl)ethyl chloride (13) was isolated by column chromatography and identified by NMR and IR analyses.

The identification data of the resultant product are as follows:

IR (neat, νmax cm$^{-1}$): 2940, 2880, 1680, 1630, 1610.

NMR (60 MHz, in CDCl$_3$, δppm): 2.8–3.8 (4H, m, C$\underline{H}_2$C$\underline{H}_2$Cl), 4.06 (3H, s, —OC$\underline{H}_3$), 6.00 (2H, s,

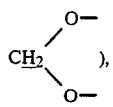

), 6.45 (1H, s,

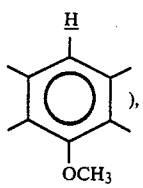

), 10.30 (1H, s, —C$\underline{H}$O).

REFERENCE EXAMPLE 1

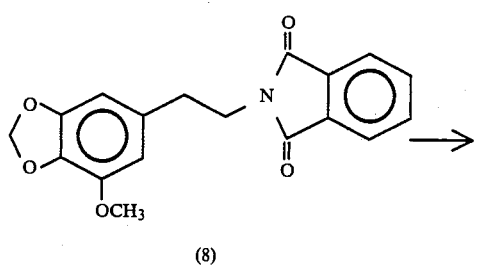

(8)

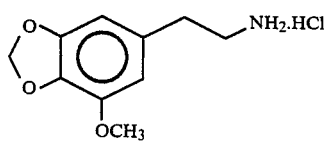

949 mg (2.92 mmol) of N-[2-(3-methoxy-4,5-methylenedioxyphenyl)ethyl]phthalimide (8) and 0.24 g (3.8 mmol) of 80% hydrazine hydrate were added to 15 ml to 15 ml of methanol and refluxed under heating for 4.5 hours. Then 15 ml of water was added to the mixture and most of methanol was distilled off under reduced pressure. Further, 7 ml of water and 2 ml of concentrated hydrochloric acid were added to the mixture, which was then refluxed under heating for 1 hour and 50 minutes. After cooling, the reaction mixture was made basic with 25% sodium hydroxide aqueous solution and extracted with 30 ml and 20 ml of ethyl acetate successively. The ethyl acetate layer was washed with 2×20 ml of a saturated saline solution, dried over anhydrous sodium sulfate and concentrated under reduced pressure. Hydrogen chloride solution in methanol was added to the residual oil. The resulting solution was concentrated and the residue was recrystallized from ethanol/ethyl ether to obtain 550 mg of 2-(3-methoxy-4,5-methylenedioxyphenyl)ethylamine hydrochloride as a crystal. Yield: 81%; melting point: 162°–164° C.

IR data of the resultant product are as follows:

IR (KBr, νmax cm$^{-1}$): 2990, 1640, 1520, 1135, 1100.

REFERENCE EXAMPLE 2

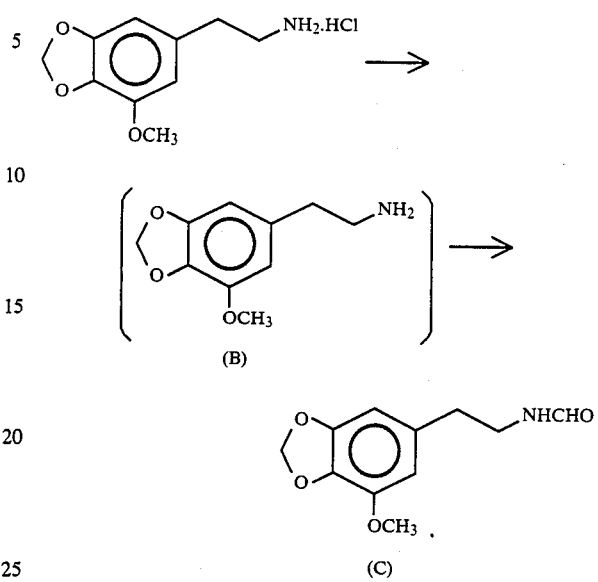

(B)

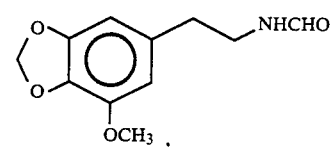

(C)

6.95 g (30 mmol) of 2-(3-methoxy-4,5-methylenedioxyphenyl)ethylamide hydrochloride was dissolved in 30 ml of water, and the mixture was made basic with 25% sodium hydroxide aqueous solution. The mixture was extracted with 30 ml of toluene. The toluene layer was washed with 10 ml of water, added with 2.73 g (59.3 mmol) of formic acid, refluxed under heating for 2 hours at normal pressure to distill off about 15 ml of the toluene while separating the produced water by an azeotropic distillation and then cooled. The deposited crystal was filtered out, washed with 3 ml of toluene and dried to obtain 5.48 g of N-[2-(3-methoxy-4,5-methylenedioxyphenyl)ethyl]formamide (C). Yield: 83%; melting point: 108°–110° C.

REFERENCE EXAMPLE 3

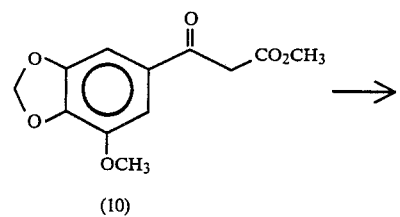

(10)

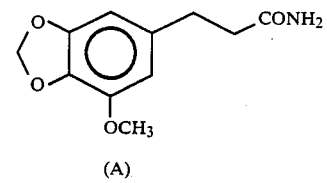

(A)

2.0 g (7.93 mmol) of methyl 3-methoxy-4,5-methylenedioxybenzoylacetate (10), 100 mg of 5% Pd/C and 50 mg of concentrated sulfuric acid were put into a 100 ml microbomb together with 18 ml of methanol and stirred at room temperature under a hydrogen pressure of 7 atm. to effect a reducing reaction. 6 hours later, ammonia gas was blown into the reaction mixture so as to saturate it with ammonia while cooling the microbomb on a bath at −25° C. After the reaction mixture was left at 55° C. overnight (the pressure reaching about 10 atm.), ammonia was distilled off and the catalyst was filtered out, followed by washing the residual solution. The resulting methanol solution was concentrated methylenedioxyphenyl)propionimide (A) as a crystal (melting point: 122°–124° C.).

REFERENCE EXAMPLE 4

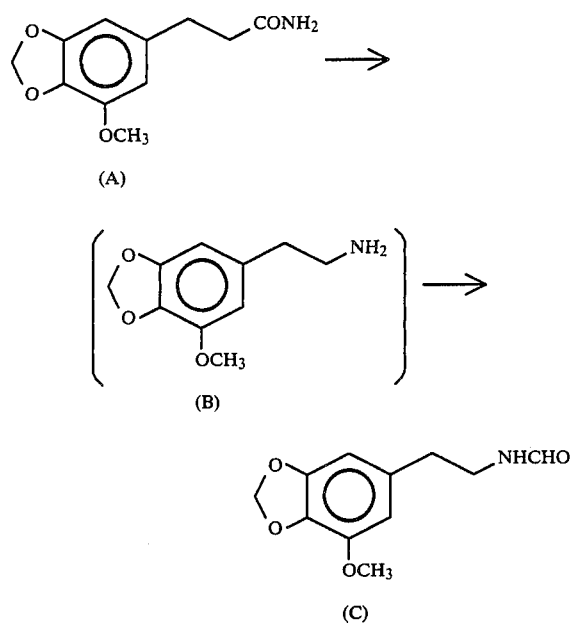

892.8 mg (4.0 mmol) of 3-(3-methoxy-4,5-methylenedioxyphenyl)propionimide (A) was added to a mixture of 3.2 ml of 5N sodium hydroxide aqueous solution and 2.7 ml of 10% sodium hypochlorite aqueous solution and stirred at room temperature. A substantially homogeneous solution was formed in about 30 minutes. This mixture was then added with 6 ml of 50% potassium hydroxide aqueous solution and further stirred in a bath at 70° C. so as to yield a light-brown oily product. One hour thereafter, the reaction mixture was cooled to room temperature and extracted with 2×10 ml of toluene. The toluene layer was washed with water, dried and added with 0.5 ml of formic acid, followed by being refluxed under heating so as to distill off the toluene at normal pressure, while separating the produced water by an azeotropic distillation. The deposited crystal was filtered out, washed with toluene and dried to obtain 720.0 mg (80.7% yield) of N-2-(3-methoxy-4,5-methylenedioxyphenyl)ethyl]formamide (B) as a crystal (melting point: 108°–110° C.).

REFERENCE EXAMPLE 5

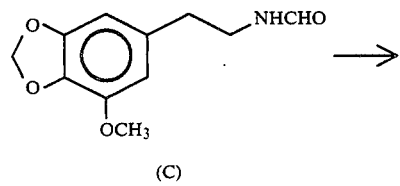

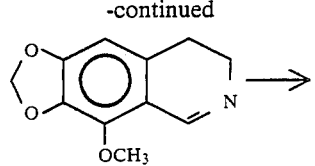

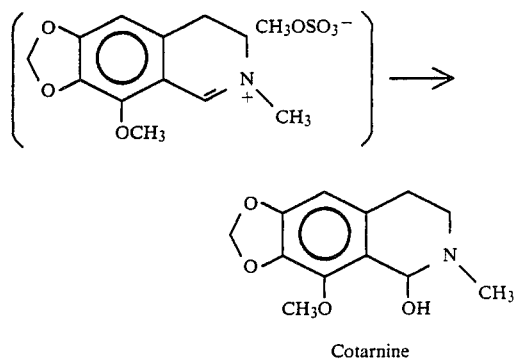

2.23 g (10 mmol) of N-[2-(3-methoxy-4,5-methylenedioxyphenyl)ethyl]formamide (C) was dissolved in 25.5 ml of methylene chloride, and to this mixture was added 1.87 ml (20 mmol) of phosphorus oxychloride. The resulting mixture was refluxed under heating for 7 hours and concentrated under reduced pressure. The residue was added with 50 ml of toluene and 50 ml of water, then further added with 14 ml of 20% sodium hydroxide aqueous solution, stirred under heating at 100° C. for one hour and cooled. The reaction mixture was separated and the aqueous layer was extracted with 25 ml of toluene. The toluene layers were combined, washed with 25 ml of water and dried over anhydrous magnesium sulfate. Distillation off the solvent gave 2.00 g of 8-methoxy-6,7-methylenedioxy-3,4-dihydroisoquinoline (D) (yield: 98%).

2.00 g (9.76 mmol) of 8-methoxy-6,7-methylenedioxy-3,4-dihydroisoquinoline (D) thus obtained was dissolved in 30 ml of toluene containing 1.35 g (10.7 mmol) of dimethylsulfuric acid. The mixture was left overnight. The deposited crystal was extracted with 20 ml of water. After a small quantity of impurities was filtered out, the aqueous solution was added with 15 g of 17% potassium hydroxide aqueous solution under ice-cooling. The resulting solution was stirred at room temperature for 40 minutes and the deposited crystal was filtered out, washed with 4 ml of water and dried to obtain 1.868 g of cotarnine with a yield of 81%.

What we claim is:

1. An anisole derivative represented by the following formula (I):

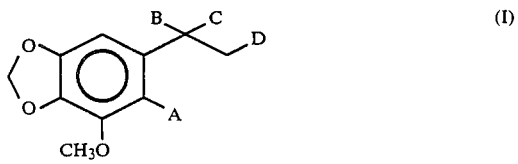

wherein:
(1) A, B and C are each a hydrogen atom, D represents —OH, a halogen atom, —CO$_2$R$^1$ of which R$^1$ represents a lower alkyl group, —OSO$_2$R$^2$ of which R$^2$ represents a lower alkyl group, or

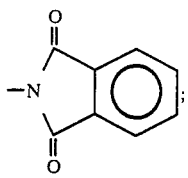

or (2) A and C are each a hydrogen atom, B is —OH, D represedents —CO$_2$R$^3$ of which R$^3$ represents a lower alkyl group; or (3) A is a hydrogen atom, B and C form an oxo group =O together, D represents —CO$_2$R$^4$ of which R$^4$ represents a lower alkyl group; or (4) B and C are each a hydrogen atom, D is a halogen atom, A represents —CHO.

2. The anisole derivative according to claim 1 wherein each of R$^1$ to R$^4$ represents a lower alkyl group of 1 to 5 carbon atoms.

3. The anisole derivative according to claim 2 wherein each of R$^1$ to R$^4$ represents a lower alkyl group of 1 to 3 carbon atoms.

4. The anisole derivative according to claim 1 which is 2-(3-methoxy-4,5-methylenedioxyphenyl)ethyl alcohol.

5. The anisole derivative according to claim 1 which is 2-(3-methoxy-4,5-methylenedioxyphenyl)ethyl methanesulfonate.

6. The anisole derivative according to claim 1 which is 2-(3-methoxy-4,5-methylenedioxyphenyl)ethyl chloride.

7. The anisole derivative according to claim 1 which is 2-(3-methoxy-4,5-methylenedioxyphenyl)ethyl bromide.

8. The anisole derivative according to claim 1 which is 2-(3-methoxy-4,5-methylenedioxyphenyl)ethyl iodide.

9. The anisole derivative according to claim 1 which is N-[2-(3-methoxy-4,5-methylenedioxyphenyl)ethyl]-phthalimide.

10. The anisole derivative according to claim 1 which is methyl 3-(3-methoxy-4,5-methylenedioxyphenyl)propionate.

11. The anisole derivative according to claim 1 which is methyl 3-hydroxy-3-(3-methoxy-4,5-methylenedioxyphenyl)propionate.

12. The anisole derivative according to claim 1 which is methyl 3-methoxy-4,5-methylenedioxybenzoylacetate.

13. The anisole derivative according to claim 1 which is 2-(2-formyl-3-methoxy-4,5-methylenedioxyphenyl)-ethyl chloride.

* * * * *